(12) United States Patent
Agrawal et al.

(10) Patent No.: US 7,842,128 B2
(45) Date of Patent: Nov. 30, 2010

(54) TISSUE MARKING COMPOSITIONS

(75) Inventors: Satish Agrawal, Concord, MA (US); Roger Boggs, Lowell, MA (US)

(73) Assignee: Performance Indicatior LLC, Lowell, MA (US)

( * ) Notice: Subject to any disclaimer, the term of this patent is extended or adjusted under 35 U.S.C. 154(b) by 417 days.

(21) Appl. No.: 11/898,569

(22) Filed: Sep. 13, 2007

(65) Prior Publication Data

US 2009/0071365 A1    Mar. 19, 2009

(51) Int. Cl.
C09D 11/00    (2006.01)

(52) U.S. Cl. .................................................. 106/31.03

(58) Field of Classification Search ............... 106/31.03
See application file for complete search history.

(56) References Cited

U.S. PATENT DOCUMENTS

| | | |
|---|---|---|
| 2,522,704 A | 9/1950 | Laval |
| 2,527,365 A | 10/1950 | Leverenz |
| 2,787,558 A | 4/1957 | Wadely |
| 3,022,189 A | 2/1962 | Malmquist |
| 3,212,898 A | 10/1965 | Gerreta |
| 3,508,810 A | 4/1970 | Baltzer |
| 3,522,143 A | 7/1970 | Motter |
| 3,560,211 A | 2/1971 | Fotland |
| 3,562,172 A | 2/1971 | Ono |
| 3,578,602 A | 5/1971 | Ono |
| 3,595,804 A | 7/1971 | Martin, Jr. |
| 3,627,690 A | 12/1971 | Casella |
| 3,650,812 A | 3/1972 | Nordstrom et al. |
| 3,654,190 A | 4/1972 | Levine |
| 3,666,352 A | 5/1972 | Wagner et al. |
| 3,668,189 A | 6/1972 | Goetz |
| 3,679,598 A | 7/1972 | Alburger |
| 3,714,181 A | 1/1973 | Lantos |
| 3,738,299 A | 6/1973 | Packler et al. |
| 3,873,390 A | 3/1975 | Cornell et al. |
| 3,884,697 A | 5/1975 | Inove |
| 3,912,677 A | 10/1975 | Baker et al. |
| 3,924,027 A | 12/1975 | Saito |
| 3,936,970 A | 2/1976 | Hodges |
| 3,957,678 A | 5/1976 | Dikhoff |
| 3,980,602 A | 9/1976 | Jakubauskas |

(Continued)

FOREIGN PATENT DOCUMENTS

EP    0 159 678 A    10/1985

(Continued)

OTHER PUBLICATIONS

U.S. National Cancer Institute SEER training module. Layers of the Skin. Accessed Aug. 20, 2008.

(Continued)

*Primary Examiner*—Helene Klemanski
(74) *Attorney, Agent, or Firm*—Burns & Levinson LLP; Orlando Lopez

(57) ABSTRACT

Provided are permanent tissue markings comprising at least one colored compound comprising a thermally activatable fragmentation group and at least one infrared absorbing compound, wherein the at least one colored compound is capable of being rendered colorless by unimolecular fragmentation of the thermally activatable fragmentation group when the tissue marking is non-imagewise exposed by a source of infrared radiation.

10 Claims, 7 Drawing Sheets

D – Sp – Nu – FG

U.S. PATENT DOCUMENTS

| | | |
|---|---|---|
| 4,025,661 A | 5/1977 | Moscony |
| 4,028,118 A | 6/1977 | Nakasuji et al. |
| 4,105,583 A | 8/1978 | Glover et al. |
| 4,121,011 A | 10/1978 | Glover et al. |
| 4,130,760 A | 12/1978 | Fanselow et al. |
| 4,188,449 A | 2/1980 | Lu et al. |
| 4,208,300 A | 6/1980 | Grauisse |
| 4,210,953 A | 7/1980 | Stone |
| 4,211,813 A | 7/1980 | Gravisse |
| 4,215,010 A | 7/1980 | Chu et al. |
| 4,268,134 A | 5/1981 | Gulati et al. |
| 4,286,957 A | 9/1981 | Le Naour-Sene |
| 4,287,229 A | 9/1981 | Watanabe |
| 4,289,497 A | 9/1981 | Hovey |
| 4,304,833 A | 12/1981 | Foley |
| 4,342,668 A | 8/1982 | Hovey et al. |
| 4,362,799 A | 12/1982 | Kondo et al. |
| 4,375,373 A | 3/1983 | Abe et al. |
| 4,379,100 A | 4/1983 | Salisbury et al. |
| 4,421,560 A | 12/1983 | Kito et al. |
| 4,425,161 A | 1/1984 | Shibahashi |
| 4,425,377 A | 1/1984 | Deal et al. |
| 4,440,672 A | 4/1984 | Chu |
| 4,451,504 A | 5/1984 | Gallaro et al. |
| 4,567,019 A | 1/1986 | Lawton |
| 4,602,263 A | 7/1986 | Borror et al. |
| 4,617,468 A | 10/1986 | Shiraishi et al. |
| 4,629,583 A | 12/1986 | Goguen |
| 4,637,698 A | 1/1987 | Kwak et al. |
| 4,663,214 A | 5/1987 | Coburn, Jr. |
| 4,681,791 A | 7/1987 | Shibahashi et al. |
| 4,695,336 A | 9/1987 | Coburn, Jr. |
| 4,698,296 A | 10/1987 | Lewis |
| 4,699,473 A | 10/1987 | Chu |
| 4,717,710 A | 1/1988 | Shimizu et al. |
| 4,717,770 A | 1/1988 | Sato et al. |
| 4,720,356 A | 1/1988 | Chu |
| 4,729,907 A | 3/1988 | Deal et al. |
| 4,734,295 A | 3/1988 | Liu |
| 4,759,453 A | 7/1988 | Paetzold |
| 4,781,647 A | 11/1988 | Doane |
| 4,818,096 A | 4/1989 | Heller et al. |
| 4,826,550 A | 5/1989 | Shimizu |
| 4,826,977 A | 5/1989 | Heller et al. |
| 4,830,875 A | 5/1989 | Lindmayer |
| 4,835,475 A | 5/1989 | Hanakura et al. |
| 4,837,141 A | 6/1989 | Kohno et al. |
| 4,857,228 A | 8/1989 | Kabay et al. |
| 4,880,667 A | 11/1989 | Welch |
| 4,884,860 A | 12/1989 | Brown |
| 4,898,895 A | 2/1990 | Masuoke et al. |
| 4,910,252 A | 3/1990 | Yonehara et al. |
| 4,913,544 A | 4/1990 | Rickwood |
| 4,921,727 A | 5/1990 | Datta et al. |
| 4,927,180 A | 5/1990 | Trundle et al. |
| 4,943,896 A | 7/1990 | Johnson |
| 4,948,210 A | 8/1990 | Simms |
| 5,007,647 A | 4/1991 | Gulick |
| 5,023,015 A | 6/1991 | Lagos |
| 5,045,706 A | 9/1991 | Tanaka et al. |
| 5,066,818 A | 11/1991 | Gemert et al. |
| 5,132,043 A | 7/1992 | Deboer |
| 5,132,045 A | 7/1992 | Osaka et al. |
| 5,135,591 A | 8/1992 | Vockel |
| 5,149,568 A | 9/1992 | Beck |
| 5,176,905 A | 1/1993 | Ohno et al. |
| 5,185,390 A | 2/1993 | Fischer et al. |
| 5,219,625 A | 6/1993 | Matsunami et al. |
| 5,221,288 A | 6/1993 | Kamata |
| 5,223,330 A | 6/1993 | Vockel |
| 5,248,916 A | 9/1993 | Tong et al. |
| 5,260,252 A | 11/1993 | Frangie |
| 5,292,549 A | 3/1994 | Van Ooij et al. |
| 5,294,375 A | 3/1994 | Waller et al. |
| 5,321,069 A | 6/1994 | Owens |
| 5,344,191 A | 9/1994 | Chang |
| 5,352,649 A | 10/1994 | Shibahashi et al. |
| 5,356,149 A | 10/1994 | Kane |
| 5,378,897 A | 1/1995 | Suzuki |
| 5,387,458 A | 2/1995 | Pavelka et al. |
| 5,389,093 A | 2/1995 | Howell |
| 5,391,327 A | 2/1995 | Ligas |
| 5,395,673 A | 3/1995 | Hunt |
| 5,409,797 A | 4/1995 | Hosoi et al. |
| 5,424,006 A | 6/1995 | Murayama et al. |
| 5,427,415 A | 6/1995 | Chang |
| 5,435,994 A | 7/1995 | Valenty |
| 5,439,785 A | 8/1995 | Boston et al. |
| 5,445,611 A | 8/1995 | Eppstein et al. |
| 5,446,150 A | 8/1995 | Rickwood |
| 5,480,482 A | 1/1996 | Novinson |
| 5,490,344 A | 2/1996 | Bussiere |
| 5,536,046 A | 7/1996 | Chang |
| 5,558,187 A | 9/1996 | Aberle |
| 5,581,090 A | 12/1996 | Goudjil |
| 5,605,734 A | 2/1997 | Yeh |
| 5,607,621 A | 3/1997 | Ishihara |
| 5,618,063 A | 4/1997 | Chang |
| 5,630,869 A | 5/1997 | Amon et al. |
| 5,644,352 A | 7/1997 | Chang et al. |
| 5,658,500 A | 8/1997 | Kumar et al. |
| 5,674,437 A | 10/1997 | Geisel |
| 5,692,895 A | 12/1997 | Franzin Nia et al. |
| 5,698,301 A | 12/1997 | Yonetani |
| 5,708,181 A | 1/1998 | Hama et al. |
| 5,716,723 A | 2/1998 | Van Cleef et al. |
| 5,717,282 A | 2/1998 | Oomen et al. |
| 5,728,758 A | 3/1998 | Smith |
| 5,730,961 A | 3/1998 | Goudjil |
| 5,731,658 A | 3/1998 | Lengyel et al. |
| 5,744,233 A | 4/1998 | Optiz et al. |
| 5,753,146 A | 5/1998 | Van Gemert et al. |
| 5,770,115 A | 6/1998 | Misura |
| 5,774,997 A | 7/1998 | Gruen, Jr. |
| 5,789,015 A | 8/1998 | Gupta et al. |
| 5,789,021 A | 8/1998 | Dooms et al. |
| 5,807,265 A | 9/1998 | Itoigawa et al. |
| 5,823,891 A | 10/1998 | Winskowicz |
| 5,833,349 A | 11/1998 | Apple |
| 5,839,718 A | 11/1998 | Hase et al. |
| 5,885,482 A | 3/1999 | Asaoka et al. |
| 5,914,076 A | 6/1999 | Schloss |
| 5,914,222 A | 6/1999 | Morrison et al. |
| 5,916,541 A | 6/1999 | Stewart |
| 5,938,544 A | 8/1999 | Winskowicz |
| 5,938,554 A | 8/1999 | Moster et al. |
| 5,973,034 A | 10/1999 | Mori et al. |
| 5,975,696 A | 11/1999 | Kohan |
| 5,976,717 A | 11/1999 | Holdik et al. |
| 5,985,381 A | 11/1999 | Conner |
| 5,989,135 A | 11/1999 | Welch |
| 6,005,024 A | 12/1999 | Anders et al. |
| 6,013,122 A | 1/2000 | Klitzman et al. |
| 6,013,980 A | 1/2000 | Goel et al. |
| 6,027,810 A | 2/2000 | Dalhquist |
| 6,046,455 A | 4/2000 | Ribi et al. |
| 6,048,347 A | 4/2000 | Erdman |
| 6,060,428 A | 5/2000 | Chang |
| 6,072,000 A | 6/2000 | Harui et al. |
| 6,111,054 A | 8/2000 | Haubennestel et al. |
| 6,117,362 A | 9/2000 | Yen et al. |
| 6,130,781 A | 10/2000 | Gauvin |
| 6,139,779 A | 10/2000 | Small |
| 6,165,234 A | 12/2000 | Kanakkannatt |

| | | |
|---|---|---|
| 6,177,487 B1 | 1/2001 | Sapper et al. |
| 6,196,241 B1 | 3/2001 | Doolan |
| 6,201,057 B1 | 3/2001 | Porter |
| 6,207,077 B1 | 3/2001 | Burnell-Jones |
| 6,267,911 B1 | 7/2001 | Yen |
| 6,268,440 B1 | 7/2001 | Kudo et al. |
| 6,268,458 B1 | 7/2001 | Soane et al. |
| 6,271,333 B1 | 8/2001 | Okuhira |
| 6,277,037 B1 | 8/2001 | Winskowicz et al. |
| 6,290,873 B1 | 9/2001 | Takahashi |
| 6,294,258 B1 | 9/2001 | Gentile |
| 6,312,782 B1 | 11/2001 | Goldberg et al. |
| 6,344,233 B1 | 2/2002 | Jamil et al. |
| 6,358,160 B1 | 3/2002 | Winskowicz |
| 6,359,048 B1 | 3/2002 | Van Duynhoven |
| 6,375,864 B1 | 4/2002 | Phillips et al. |
| 6,391,492 B1 | 5/2002 | Kawakanii et al. |
| 6,465,791 B1 | 10/2002 | Ribi et al. |
| 6,499,995 B1 | 12/2002 | Schwartz |
| 6,500,555 B1 | 12/2002 | Khaldi |
| 6,508,732 B1 | 1/2003 | Romberger et al. |
| 6,514,594 B1 | 2/2003 | Wei et al. |
| 6,553,696 B1 | 4/2003 | Foster, Sr. |
| 6,572,784 B1 | 6/2003 | Coombs et al. |
| 6,596,816 B1 | 7/2003 | Haubennestel et al. |
| 6,599,444 B2 | 7/2003 | Burnell-Jones |
| 6,617,468 B2 | 9/2003 | Haubennestel et al. |
| 6,623,382 B2 | 9/2003 | Winskowicz |
| 6,623,791 B2 | 9/2003 | Sadvary et al. |
| 6,638,160 B2 | 10/2003 | Yoshitomi |
| 6,660,184 B2 | 12/2003 | Singh et al. |
| 6,660,324 B2 | 12/2003 | O'Rourke et al. |
| 6,710,127 B2 | 3/2004 | Haubennestel et al. |
| 6,726,915 B2 | 4/2004 | Livoreil et al. |
| 6,746,724 B1 | 6/2004 | Robertson et al. |
| 6,750,266 B2 | 6/2004 | Bentsen et al. |
| 6,773,628 B2 | 8/2004 | Kinno |
| 6,800,122 B2 * | 10/2004 | Anderson et al. ........ 106/31.03 |
| 6,800,684 B2 | 10/2004 | Hayashi et al. |
| 6,807,909 B1 | 10/2004 | Coots |
| 6,814,760 B2 * | 11/2004 | Anderson et al. ........ 106/31.03 |
| 6,818,310 B2 | 11/2004 | Namiki et al. |
| 6,833,191 B2 | 12/2004 | Bayless |
| 6,861,467 B2 | 3/2005 | Nakano |
| 6,870,024 B2 | 3/2005 | Haubennestel et al. |
| 6,878,076 B2 | 4/2005 | Winskowicz |
| 6,894,124 B2 | 5/2005 | Matsuno et al. |
| 6,905,634 B2 | 6/2005 | Burnell-Jones |
| 6,953,536 B2 | 10/2005 | Yen et al. |
| 7,033,712 B2 | 4/2006 | Liang |
| 7,050,387 B2 | 5/2006 | Tsujita et al. |
| 7,087,710 B2 | 8/2006 | Medsker |
| 7,175,950 B2 * | 2/2007 | Anderson et al. ........ 106/31.03 |
| 7,285,364 B2 * | 10/2007 | Anderson et al. ........ 106/31.03 |
| 2002/0034475 A1 | 3/2002 | Ribi |
| 2002/0068166 A1 | 6/2002 | Senga et al. |
| 2003/0219531 A1 | 11/2003 | Parsapour |
| 2003/0222247 A1 | 12/2003 | Putman et al. |
| 2004/0009833 A1 | 1/2004 | Selevan |
| 2004/0033352 A1 | 2/2004 | Massa et al. |
| 2004/0169474 A1 | 9/2004 | Hampden-Smith et al. |
| 2004/0187417 A1 | 9/2004 | Thomas |
| 2005/0031838 A1 | 2/2005 | Lagunowich et al. |
| 2005/0172852 A1 | 8/2005 | Anderson et al. |
| 2005/0224764 A1 | 10/2005 | Ma et al. |
| 2005/0235848 A1 | 10/2005 | Butland |
| 2007/0107625 A1 | 5/2007 | Anderson et al. |
| 2009/0076535 A1 * | 3/2009 | Agrawal et al. ............. 606/186 |

FOREIGN PATENT DOCUMENTS

| | | |
|---|---|---|
| EP | 0 311 157 B1 | 4/1989 |
| EP | 0 318 999 B1 | 6/1989 |
| EP | 0 417 490 B1 | 3/1991 |
| EP | 0 438 836 B1 | 7/1991 |
| EP | 0 825 249 B1 | 2/1995 |
| EP | 0 713 894 B1 | 5/1996 |
| EP | 0 838 475 B1 | 4/1998 |
| EP | 0 851 452 B1 | 7/1998 |
| EP | 0 977 167 A1 | 2/2000 |
| EP | 1 028 001 B1 | 8/2000 |
| EP | 1 176 575 A1 | 1/2002 |
| EP | 1 283 106 A1 | 2/2003 |
| EP | 1 306 872 A2 | 5/2003 |
| EP | 1 514 910 A1 | 3/2005 |
| GB | 2153804 A | 8/1985 |
| JP | 60-032234 A | 2/1985 |
| JP | 1249436 A | 10/1989 |
| JP | 403261596 | 11/1991 |
| JP | 404358145 A | 12/1992 |
| JP | 9-132648 A | 5/1997 |
| JP | 2000294130 A | 10/2000 |
| JP | 2001-329047 A | 11/2001 |
| WO | WO 88/07903 | 10/1988 |
| WO | WO 01/10551 A1 | 2/2001 |
| WO | WO 01/79360 A1 | 10/2001 |
| WO | WO 02/31065 A3 | 4/2002 |
| WO | WO 02/098993 A1 | 12/2002 |
| WO | WO 02/098995 A1 | 12/2002 |
| WO | WO 03/018651 A1 | 3/2003 |
| WO | WO 03/044092 A3 | 5/2003 |
| WO | WO 2004/075624 A3 | 9/2004 |
| WO | WO 2004/112482 A2 | 12/2004 |
| WO | WO 2005/017048 A3 | 2/2005 |
| WO | WO 2005/018370 A1 | 3/2005 |
| WO | WO 2005/029163 A1 | 3/2005 |
| WO | WO 2005/035461 A1 | 4/2005 |
| WO | WO 2005/063484 A1 | 7/2005 |
| WO | WO 2005/066278 A1 | 7/2005 |
| WO | WO 2005/066995 A3 | 7/2005 |

OTHER PUBLICATIONS

C.J. Bartelson and F. Grum, "Optical Radiation Measurements: vol. 5—Visual Measurements," Academic Press, Inc. (1984).

Yen and Weber, "Inorganic Phosphors—Compositions, Preparation and Optical Properties," CRC Press (2004).

* cited by examiner $$D - Sp - Nu - FG$$

Figure 1

TISSUE MARKING COMPOSITIONS

BACKGROUND OF INVENTION

This invention relates generally to tissue markings that are normally permanent, but can be erased that is, rendered colorless when desired. In particular, this invention relates to tissue marking, which can become colorless when infrared radiation is applied as well as to methods of their use.

Tattoos, which are a form of tissue markings, have been in use for thousands of years by many cultures for many purposes including artistry, beauty, identification, and religious purposes. Today the majority of tattoos are used for artistic expression as well as cosmetic applications such as permanent lip coloration, eyebrow coloration and eyeliner. Other uses for tattoos include corrective pigmentation following surgery and identification markings on animals.

The tattooing procedure consists of piercing the skin with needles or similar instruments to introduce an ink that typically includes particles of pigment suspended in a liquid carrier. Pigment particles that do not enter the dermis (larger pigment particles) and remain in the epidermis are sloughed off over time, whereas enough of the particles (smaller particles) that get lodged in the dermis are phagocytosed by dermal cells or retained in the extracellular matrix to create permanent markings. It should be noted that some of the ink particles in the dermis, particularly the minute particles may potentially be removed and/or relocated by the body's biological processes. Thus, a permanent tattoo is created when a sufficient number of pigment particles introduced into the body are retained in the dermis. Typical tattoo pigments include carbon black, inorganic metal salts and colored organometallic complexes.

Tattoos or tissue marking ingredients have not yet been regulated or fully disclosed to the public and have been known to cause allergic reactions which in some cases can be severe even well after the time of tattooing, or after exposure to sunlight or laser treatments. Despite the fact that there is a paucity of data in the literature concerning the toxicity and carcinogenicity of tissue markings as well as their long their long term effects on the body, they continue to be used today.

Statistics have shown that a large portion of people who have tattoos wish to have them removed. Since tattoos are generally designed to be permanent, their removal is very difficult. Overtattooing, dermabrasion, and surgical excision are typical "removal" methods as well as the more current method of using pulsed lasers. In laser removal; intense pulses of laser energy are specifically absorbed by the tissue marking particles. However, such methods require lasers emitting visible radiation, which consequently, depending upon the tattoo particle color and hence the wavelength of the laser radiation used, will result in absorption of the radiation by the skin and surrounding tissue, and thus cause collateral damage.

Such methods of tattoo removal can be categorized as "tattoo removal by dispersal" since the laser causes the pigment particles to break into minute particles for dispersal by the body's biological processes such as lymphatic transport system and/or immune processes. Using laser techniques to remove tattoos that utilize current tissue marking compositions have a number of disadvantages. Because of the reliance on "tattoo removal by dispersion", the body is not only exposed to additional health hazards but also multiple treatments are required which are not only expensive but can be painful. Additionally, multiple lasers are needed for multicolored tattoos, while some pigments such as green and yellow are virtually impossible to remove.

U.S. Pat. No. 6,013,122 discloses removable tissue markings wherein pigment or dye particles are immobilized by a vehicle which surrounds such dye or pigment, that is, the colored particles are encapsulated in said vehicle and implanted into the skin. The vehicle, encasing the dye or pigment, ruptures when exposed to specific forms of energy, such as UV light or infrared energy and the pigment or dye is dispersed or dissipated ("tattoo removal by dispersal") from the location in which it was administered, therefore erasing the tattoo image. It should be noted that tattoo removal by dispersal necessitates the colored particles to be small so that they can be dispersed to erase the tissue marking, which in turn requires the colored particles to be encapsulated, for otherwise, the tissue marking would not be permanent. As stated above "tattoo removal by dispersal" of the colored particles is inherently risky, as the body could be subjected to allergic or toxic reactions. If the colored compound is chosen to be biocompatible, then the choice of suitable dues will be significantly narrowed. Thus, the requirement of biocompatibility will significantly narrow the choice of suitable dyes. It should be noted that the above invention does not envision tattoo removal by rendering the dye or pigment colorless.

U.S. Pat. No. 6,814,760 provides for microparticles that create permanent tissue markings, such as tattoos, designed in advance for change and/or removal on demand, as well as methods for implanting the microparticles in tissue and methods to change and/or remove the implanted markings. The microparticles contain chromophores (colored particles) which are encapsulated by coating materials by a variety of encapsulation techniques such as aerosol collision, chamber deposition etc.

Two embodiments for the removable tissue marking compositions, which are in the form of microparticles, are envisioned. In the first embodiment, microparticles which contain chromophores (colored compound particles) are constructed such that tattoo removal is accomplished by dispersal of the colored compound particles, that is, the dispersal is achieved by making the microparticles permeable, such as by rupture of the coating comprising the microparticle. The chromophore (colored particles) is dispersed either by dissolution in bodily fluids, or by biological processes such as metabolism, lymphatic transport etc. It should be noted that tattoo removal by dispersal necessitates the colored particles to be small so they can be dispersed to erase the tissue marking which in turn requires the colored particles to be encapsulated, for otherwise, the tissue marking would not be permanent. Relying on dispersion as the removal technique exposes the subjects to health hazards by virtue of some of the tattoo particles entering the body such as in the lymphatic system.

In the second embodiment, microparticles can contain chromophores that are rendered invisible in-situ, that is, without rupturing the microparticles, and the chromophore does not need to be dissolved, metabolized or dispersed for removal of the marking. Thus the tissue markings can become invisible without the need for being released into the bodily fluids. This embodiment generally requires that the colored compound be selected such that it can absorb the triggering electromagnetic radiation. Lasers used to deliver the energy for tattoo removal for these bleachable chromophores would either be near UV, visible, or near infra red.

For the case wherein the tissue marking is rendered colorless with near UV energy, apart from health hazards to the subjects being exposed to such UV energy, the chromophores of such tissue markings will generally be subject to photolytic degradation, and hence, such tissue markings will be vulnerable to fading by prolonged exposure to sunlight, adversely affecting their permanence until the desire for removal.

Use of tissue markings that can be tendered colorless or bleachable by visible lasers will be similar to the current practice of tattoo removal, requiring multiple visits and, additionally, will not be devoid of tissue scarring or injury. Intense visible light can target the skin's natural pigment, melanin, resulting in temporary or permanent hypopigmentation or hyperpigmentation, especially in dark or tanned skin, and/or hair loss in the area.

The near infra red bleachable tissue markings will generally have colors in the red portion of the visible spectrum thereby severely limiting the color choices for the tissue markings.

Embodiments wherein the tissue marking is rendered colorless without rupturing the microcapsule, and not requiring the chromophore of the tissue marking to absorb the triggering radiation, that is, requiring the colored compound to contain a specific radiation absorbing component, is one wherein heat is used to release a second reactive component such as a strong acid, or strong oxidizing agent, or a thermal initiator generating free radicals which then must first come into contact with the pigment or dye and then react with it to bleach the chromophore. One can question the practice of introducing strong oxidizing/reducing agents or free radicals in the human body. Even though such materials may be encapsulated, they would pose significant health hazards since there is always a danger of leakage from the capsule. Further, such embodiments can result in fairly complex microcapsule constructions.

Thus there is a need for new, on-demand removable tissue marking compositions and methods for their use that are simple, that do not require use of hazardous materials for accomplishing the color removal, that do not require dispersal of the tissue marking for removing the marking, that is, markings wherein the color can be switched off in-situ, that embody methods of color change which do not adversely impact tattoo permanence, that minimize or eliminate the damage to the skin and surrounding tissue, and wherein the tattoo removal method would be applicable to a wide variety of colored materials.

SUMMARY OF INVENTION

The present invention provides for permanent tissue marking compositions that can be used as tissue markings which have been predesigned to be removable on demand, wherein, the tissue marking compositions do not require any other reactive species to effect color removal, that is the color change is a unimolecular reaction, and wherein markings can be removed in a single treatment by exposure to infrared radiation. There are many advantages of the inventive ink compositions of this invention. One advantage is that these compositions do not necessarily require any specialized vehicles such as encapsulated colored particles for use as permanent tissue markings. That is, the colored compositions of this invention, which comprise at least one colored particle and an infrared absorber, are not required to undergo encapsulation for use as a permanent tissue marking. A second advantage is that since color removal does not require any additional reactive species, there are no additional health hazards to deal with. A third advantage of the inventive ink compositions is that the colored particles do not have to be dispersed or removed from the tissue for color removal as the color is switched off due to non-imagewise exposure to infrared radiation. It should be noted that the now colorless, formerly colored, composition continues to exist as before in its immobilized state. A fourth advantage of the inventive ink compositions is their ability to be of any color and become colorless using the same infrared energy. A fifth advantage of the inventive ink compositions is their ability to become colorless using infrared radiation, such that the surrounding skin is substantially transparent to the infrared radiation. The present invention also includes methods of applying the inventive ink compositions and methods of rendering the ink colorless.

In a first aspect, the present invention provides for a colored composition for use as a tissue marking which includes at least one colored compound containing a thermally activated fragmentation group and at least one infrared absorbing compound in which the at least one colored compound is capable of being rendered colorless by unimolecular cleavage of the fragmentation group upon exposure of the tissue marking to a source of infrared radiation.

In a second aspect, the present invention provides for a method of applying a colored composition to a tissue by implanting into the tissue an amount of the tissue marking in sufficient quantity such that enough of the colored composition is retained in the tissue to form a permanent detectable marking until desired to be erased, said ink containing at least one colored compound containing a thermally activated fragmentation group, and at least one infrared absorbing compound wherein the at least one colored compound is capable of being rendered colorless by unimolecular cleavage of the fragmentation group upon exposure of the tissue marking to a source of infrared radiation.

In a third aspect, the present invention provides for a method of removing the tissue marking by implanting into a tissue an amount of the colored ink composition in sufficient quantity to form a detectable marking, said ink containing at least one colored compound comprising a thermally activated fragmentation group and at least one infrared absorbing compound wherein the at least one colored compound is capable of being rendered colorless by unimolecular cleavage of the fragmentation group upon exposure of the tissue marking to a source of infrared radiation and applying infrared radiation to a sufficient amount of the tissue marking to render the ink colorless.

BRIEF DESCRIPTION OF THE DRAWINGS

FIG. 1 provides a general representative structure of a functionalized colored compound useful for the current invention.

DETAILED DESCRIPTION OF THE INVENTION

Figure 2A:
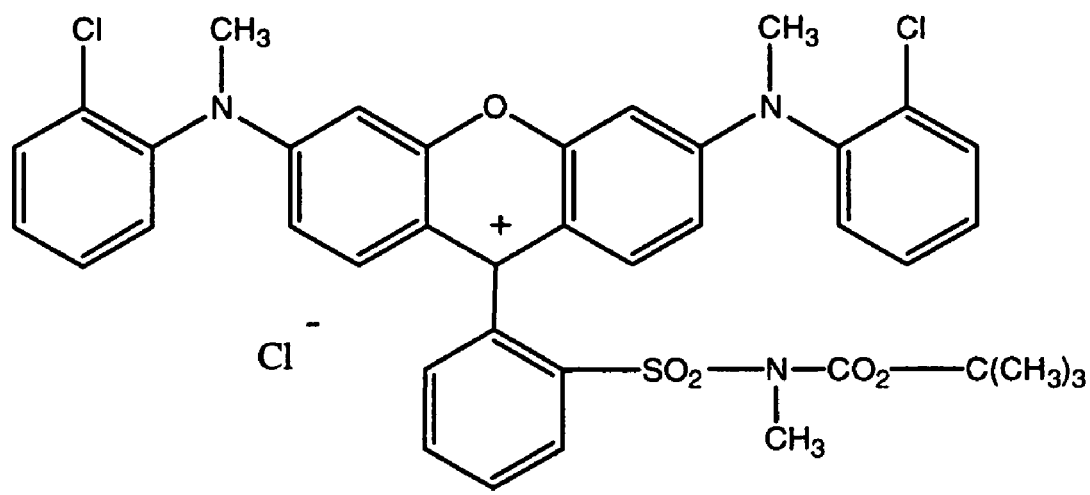
FIG. 2A depicts the structure of a magenta colored compound suitable for the present invention.

The present invention provides for permanent tissue marking compositions, which are pre-designed to be permanent until the desire for removal, that is, removable on demand, and transition to a colorless state by application of non-imagewise infrared radiation.

As used herein the term "colored compound" refers to dyes and pigments that are visible to the unaided eye under normal lighting conditions such as in diffuse sunlight or standard artificial lighting.

The term "dye", as used herein, refers to a material, which contains a chromophore that allows the material to be visible to the unaided eye under normal lighting conditions.

As used herein, the term "colorless" refers to that state of a colored compound wherein, relative to the original color, the color is reduced by a minimum of 60% in the colorless state.

A "chromophore", as used herein, refers to the part of a molecule responsible for its color.

As used herein an "indispersible substance" refers to particulate matter used for tissue markings that is on average large enough such that a sufficient number of the particles are retained when injected into the body to form a permanent tissue marking, that is, a sufficient number of the particles do not disintegrate, dissolve, become metabolized in tissue or relocated/eliminated by the body's biological processes. It should be noted that some number of the individual microparticles may be relocated from the tissue marking site through biological processes (such as lymphatic transport).

As used herein a "colored composition" refers to an admixture of at least one indispersible colored compound and one indispersible infrared absorber to render a tissue marking As used herein a "tissue marking" comprises a colored composition which after implantation into the tissue results in a permanent marking in the tissue until such time it is desired to be removed. Tissues are inclusive of including skin, iris, sclera, dentin, fingernails, toenails, tissue beneath fingernails, tissue beneath toenails, tissue inside the mouth, and tissue lining internal body passages.

As used herein, the term "thermally activated" refers to the property of a material that undergoes change when exposed to a particular temperature.

The term "trigger", as used herein, refers to the thermally activated portion of a fragmentation group. The trigger may be a part or the entire thermally activated fragmentation group.

As used herein, "fragmentation" refers to the cleavage of a molecule by the scission of one or more chemical bonds.

The term "unimolecular fragmentation", as used herein, refers to the cleavage of a single molecule by scission of one or more chemical bonds, caused without the interaction or involvement of a secondary molecule.

The term "nucleophilic group", as used herein, refers to a group containing a free pair of electrons that are capable of reacting.

The term "internal cyclization" refers to a reaction in which a substituent on a molecule undergoes a reaction with the said molecule resulting in a cyclic product.

The term "ballast group" refers to a group attached to a molecule to tailor into the molecule desired characteristics such as to retard the mobility of a molecule or portions thereof, such mobility emanating from either chemical or physical interactions or both or to impart biocompatibility or both, or to aid in the ability to formulate the composition or the like.

As used herein, the term "binder" refers to a material, generally a polymeric species, that is used to make various components in a composition reside together in proximity As used herein, a "biologically inert" material refers to materials which have no significant biological effect when implanted into the body.

As used herein, a "biocompatible material" refers to materials which have no significant adverse biological effect when implanted into the body.

As used herein "non-imagewise exposure" refers to an exposure, which does not differentiate between imaged and non imaged areas of a marking or image. In imagewise exposure, some areas are exposed while other areas are not to cause a differentiation between an exposed and an unexposed area, hence creating an image. Non-imagewise exposure is an exposure protocol that during the exposure step does not differentiate between the areas that have markings, or images, and areas that do not. As such non-imagewise exposure may be a broad, blanket exposure or a scanning exposure. In the current invention the non-imagewise exposure is designed to eliminate any image of the tissue marking, such that no image remains.

The present invention provides for tissue markings, and methods of their use, which are suitable as permanent tissue markings, and which are capable of having their color rendered colorless upon application of infrared radiation. The tissue markings useful in the present invention include at least one colored compound that contains or has been modified to contain a nucleophilic group as well as a thermally activatable fragmentation group, which upon fragmentation will render the colored compound colorless.

The tissue markings of this invention can be rendered colorless by a unimolecular fragmentation, that is, they do not require reaction with another compound to achieve the transition to a colorless state. It should be noted that the use of above stated concept of fragmentation to render the tissue marking colorless can result in low residual densities or d-min without requiring any strong secondary oxidizing or reducing agents. Hence, the concept of thermally triggered unimolecular fragmentation to create removable, on demand, tissue marking is of great benefit since, otherwise, the use of a second component such as a strong oxidizing or reducing agent to render the tissue marking colorless would pose a hazard to the body. Additionally the colorless species continues to exist in its immobilized state.

It should be further noted that the transition of the tissue marking to a colorless state can be accomplished by a non imagewise exposure to infrared radiation, because the areas of the body which do not have any tattoo would also not have any infrared absorber and hence will be essentially unaffected by the exposure.

The tissue markings of this invention also include those wherein a suitable ballast group is attached to the selected colored compound. The ballast groups can be selected to enhance specific characteristics of the colored compound. For example, a ballast group can be selected to further restrict the mobility of the tissue marking, or to enhance the colored compound biocompatibility, or to aid in formulating the tissue marking.

By incorporating an infrared compound whose absorption wavelength is selected such that the skin is essentially transparent to the radiation, one can minimize or eliminate damage to the skin and tissue. Hence, unlike today's practice, the tissue markings of this invention can be designed to be rendered colorless with minimal to no damage of the skin or tissue. It should also be noted that the tissue markings of this invention are rendered colorless without the dispersal of the colored compound into the human body. It is believed that when infrared radiation from an infrared radiation source, such as a laser, is applied to the tissue marking composition, the infrared absorbing compound absorbs the radiation and transfers heat to the colored compound with the attached fragmentation group in an amount sufficient to cause the cleavage of the fragmentation group with subsequent internal cyclization to render the compound colorless.

It would be advantageous to ensure proximity of the colored compound and the infrared absorbing compound within the tissue marking. Close proximity will ensure efficient heat transmission to the colored compound thereby minimizing the infrared energy required for transition to the colorless state. It should be noted that one can select the fragmentation group such that on fragmentation either the fragmented species can become gaseous and escape from the body or the fragmented species remains behind in the body. Depending on the specific fragmentation group selected, in some cases, such as the case wherein the fragmented group is left behind, it may be necessary to have a ballast group attached to the fragmentation group to ensure its immobility upon fragmentation or cleavage from the colored compound.

In general one can create a functionalized colored compound that is controlled by a trigger group, commonly referred to as a protective group, which can be removed by changes in pH, electromagnetic radiation, thermally, or under a number of other conditions. Removal of the trigger group creates a molecular cascade in which a nucleophilic atom, such as oxygen, nitrogen, sulfur, carbon, silicon, phosphorus, selenium, or their oxides, are eliminated as a result of the loss of the trigger group and the nucleophile attacks and interrupts the chromophore rendering it essentially colorless.

Examples of colored materials containing trigger groups that can be removed by alkali wherein the nucleophilic groups are oxygen- or nitrogen-based can be found in U.S. Pat. No. 4,304,833. We have found that those fragmentation groups capable of undergoing alpha-beta elimination (cited in U.S. Pat. No. 4,304,833) associated with nucleophiles that are based on oxygen or nitrogen can also be triggered by heat and hence infrared radiation. Examples of carbamate fragmentation groups associated with nitrogen based nucleophiles that are thermally triggered for use with imagewise exposure can be found in U.S. Pat. No. 4,602,263.

Figure 1:
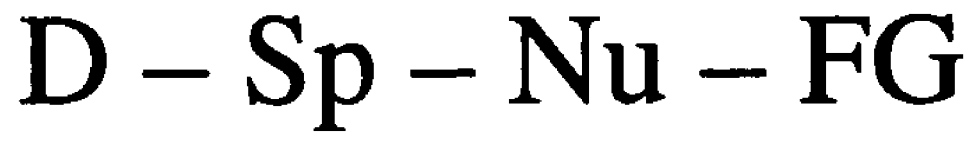

A general representative structure of a functionalized colored compound useful for the current invention is shown in FIG. 1. In FIG. 1, D is a chromophore of the colored compound, Sp is a substituted or unsubstituted optional spacer group connecting the colored compound to a nucleophile Nu, Nu is a nucleophile which can be substituted or unsubstituted, and FG is a thermally activated fragmentation group, which could be the trigger group in its entirety or may contain the trigger group as well as other species. Upon cleavage of the fragmentation group, the nucleophile enables a cyclic structure of D-Sp-Nu, which is essentially colorless.

Suitable colored compounds, represented by D in FIG. 1, include, for example, substituted and unsubstituted triarylmethane dyes, xanthene dyes, rhodamines dyes, fluoran dyes, azocarbocyanine dyes, thiazine dyes, acridine dyes and aminoanthroquinone dyes, or other dyes.

Suitable optional spacer group connecting to the colored compound, represented by Sp in FIG. 1, include, for example, substituted and unsubstituted alkyl groups such as methylene, ethylene, and propylene groups, thionyl groups, cycloaliphatic groups and the like. The Sp group is selected to facilitate the formation of a favorable ring size upon internal cyclization to render the colored compound colorless.

Suitable nucleophiles, represented by Nu in FIG. 1, include, for example, substituted or unsubstituted nucleophilic group with a free pair of electrons capable of cyclization, for example, substituted or unsubstituted nitrogen, oxygen, sulfur, phosphorus, carbon, selenium, and silicon.

Suitable thermally activatable fragmentation groups, represented by FG in FIG. 1, include, for example, substituted and unsubstituted carbonates, carbamates, esters, lactams, lactones, amides, imides, oximes, sulfonates, sulfinates, sulfenates, phosphates, and phosphonates and $—R_2C—RHC—Y$, wherein R is the same or different and comprises substituted or unsubstituted alkyl, aryl, or aralkyl groups and wherein Y is an electron withdrawing group, for example, cyano, nitro, a sulfoxide, a carbonyl containing compound, a sulfonamide or, for example, an electron withdrawing group having a positive sigma value greater than 0.6 as defined by Hammett's Equation, and other electron-withdrawing substituents that are capable of fragmenting when a sufficient amount of thermal energy is applied.

FIG. 2A depicts a magenta-colored compound suitable for the present invention. In FIG. 2A, a xanthene chromophore has attached to it an $SO_2$ spacer group, which is attached to a nucleophilic methylamine group and attached to it is a thermally activatable fragmentation t-butoxy-carbonyl group with the t-butyl being a trigger group.

Figure 2B:
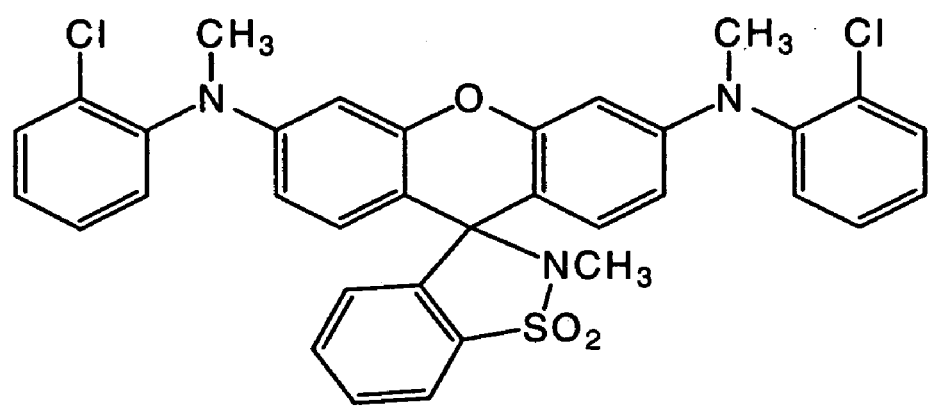
FIG. 2B depicts the structure of the colorless compound that results when the t-butyl-carbonyl group of the compound of FIG. 2A, having received sufficient thermal energy, fragments and the resultant nucleophilic nitrogen cyclizes with the chromophore.

When the compound of FIG. 2A receives sufficient thermal energy, the t-butyl-carbonyl group fragments and the resultant nucleophilic nitrogen cyclizes with the chromophore to give the colorless compound in FIG. 2B.

Figure 3:
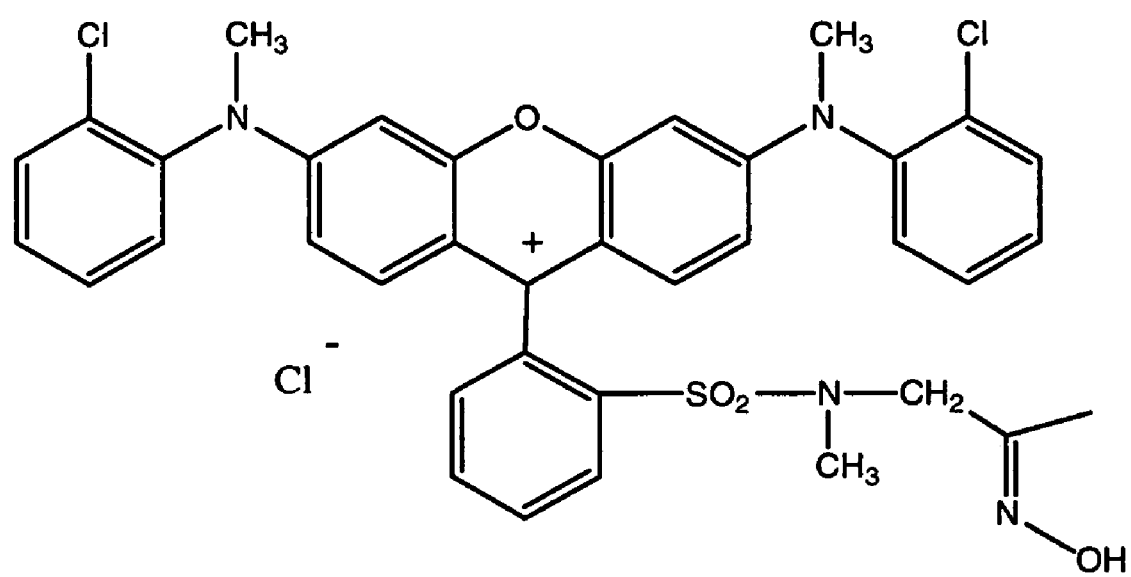
FIG. 3 represents a structure employing an oxime fragmentation group useful in lowering activation temperature.

We have also found that the thermally activatable fragmentation groups can contain trigger moieties that can be selected to adjust the kinetics of the colored to colorless transition. For example, the t-butoxy-carbonyl thermally activatable fragmentation group containing the t-butyl trigger group (—COO-t-But in FIG. 2) can be thermally activated to trigger at temperatures of approximately 160° C.-180° C. when tested by heating on a hot plate. A lower activation temperature, which would result in faster fragmentation kinetics, can be achieved by use of an oxime fragmentation group. (See FIG. 3).

Figure 4:
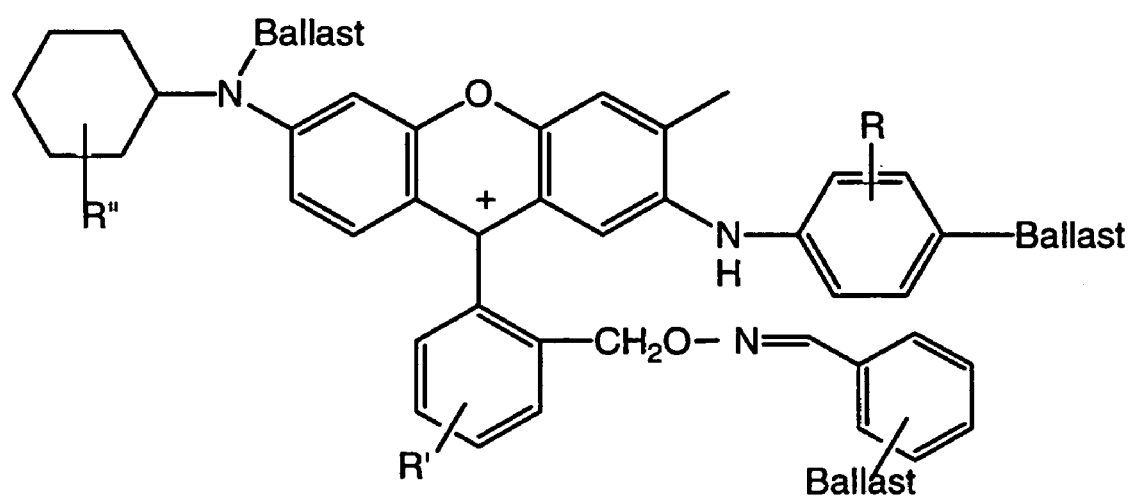
FIG. 4 represents a structure employing an oxime fragmentation group that exhibits an activation temperature of 120° C.

Colored compounds containing an oxime thermally activated fragmentation group of the type shown in FIG. 4 exhibits an activation temperature of 120° C. A higher activation temperature (hence, slower kinetics) can be achieved by use of a thermally activatable fragmentation group containing a cycloalkyl trigger group (See FIG. 5). One can adjust the kinetics of the fragmentation and hence the kinetics of the colored to colorless transition by adjusting the degree of electron withdrawing capability in the fragmentation group.

Having the ability to adjust the activation temperature that is, the temperature at which the fragmentation group cleaves at an acceptable rate, is an important design criterion for the tissue markings. It can be appreciated that to ensure permanence, the kinetics of fragmentation should be extremely low at body temperatures. This criterion would drive selection of the activation temperature towards higher values. However, too high an activation temperature will result in requiring higher amounts of infrared energy which in turn will increase vulnerability of tissue to heat damage. Hence the goal will be to select an activation temperature high enough to ensure tissue marking permanence but not require excessive amounts of energy.

The tissue marking compositions of the current invention further include infrared absorbing compounds which remain present in the permanent tissue marking. When it is desirable to "remove" the tattoo, that is, render the tattoo colorless, the infrared absorbing compound absorbs infrared radiation and the heat generated from the absorption transfers to the thermally substituent of the colored compound which then fragments. Infrared absorbing compounds that are useful for the current invention include, for example, cyanine, squarylium, azulenium, indophenol, naphthoquinone, and anthraquinone compounds. Typically these compounds have little to no absorbance in the visible region of the electromagnetic spectrum, thus causing no interference with the color of the tissue marking or when the tissue marking is rendered colorless. Examples of infrared absorbing compounds are disclosed in U.S. Pat. No. 5,409,797 herein incorporated by reference for all purposes.

As stated above, the colored compound or infrared absorbing compound may optionally have attached to it one or more ballast groups. In the case of the colored compound a ballast group may be attached to the chromophore portion, the fragmentation group, or both, or on other portions of the molecule. Ballast groups are designed to add predetermined properties to the ink where they are needed. For example, since it is important for tissue markings to be biocompatible in the dermis so as to have no significant biochemical, allergic or immune response by the body after the normal healing period, ballast groups may be attached to the components of the tissue marking to aid in biocompatibility. Ballast groups attached to infrared absorbing compound, by restricting their mobility, can assist in ensuring proximity of the colored compound and the infrared absorbing compound for high efficiency in transferring the heat to the colored compound.

One can also achieve close proximity of the colored compound and the infrared absorber by attaching affinity groups (for example to create hydrogen bonding) to the colored compound, or the infrared absorber or both. Alternatively, the colored compound and the infrared absorber can be encapsulated. It can be appreciated that closest proximity will be achieved by covalently or ionically linking the infrared absorber and the colored compound.

As stated above, the ballast group can be attached to different components of the colored compound as needed to tailor desired characteristics into the compound. For example, a ballast group may be attached to the fragmenting group to enhance its immobility after fragmentation. Another example is the ballast group could be attached to the chromophoric portion of the colored compound to further enhance its immobility in the tissue. A further example is a ballast group may be attached to any portion of the colored compound to aid in the formulation of the composition. A representative structure of a functionalized colored compound containing ballast groups useful for the current invention is shown in FIG. 6.

Figure 5:
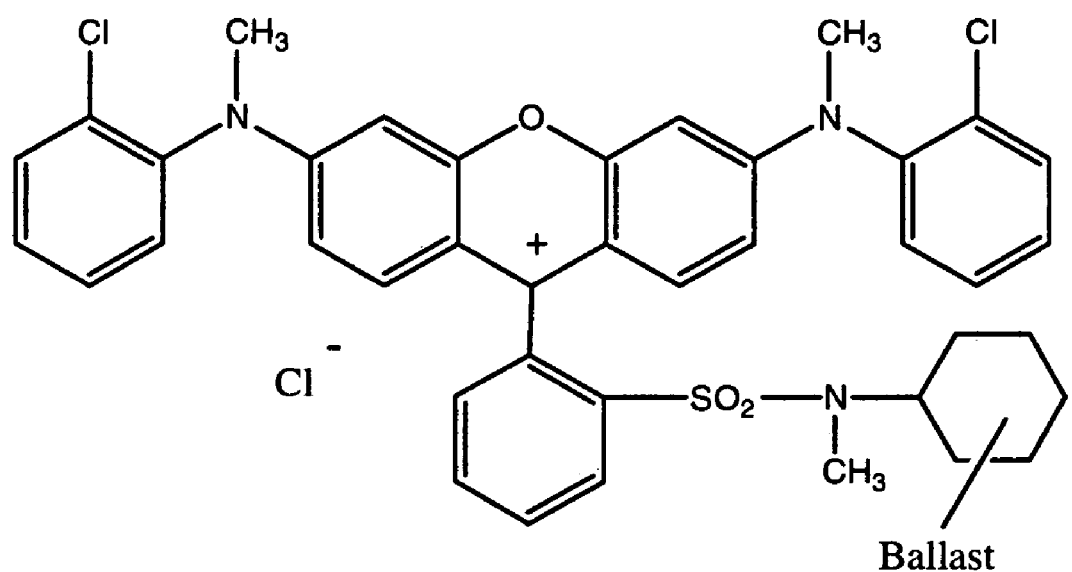
FIG. 5 represents a structure employing a cycloalkyl trigger group useful in achieving higher activation temperatures.

One or more positions on the colored compound can be substituted with one or more types of ballast groups to exhibit the desired property. The ballast groups are chosen so as not to interfere with the "removal" process, for example, by being essentially transparent to the infrared radiation. In FIG. 5 there are three ballast groups shown to illustrate useful positions, two ballast groups are attached to the chromophore of the colored compound and one ballast group is attached to the fragmentation group. Also in this example the spacer group, Sp, is methylene, the nucleophile, Nu, is oxygen and the fragmentation group, FG, is —$CH_2CH_2$—$SO_2$— Ballast.

Figure 7:
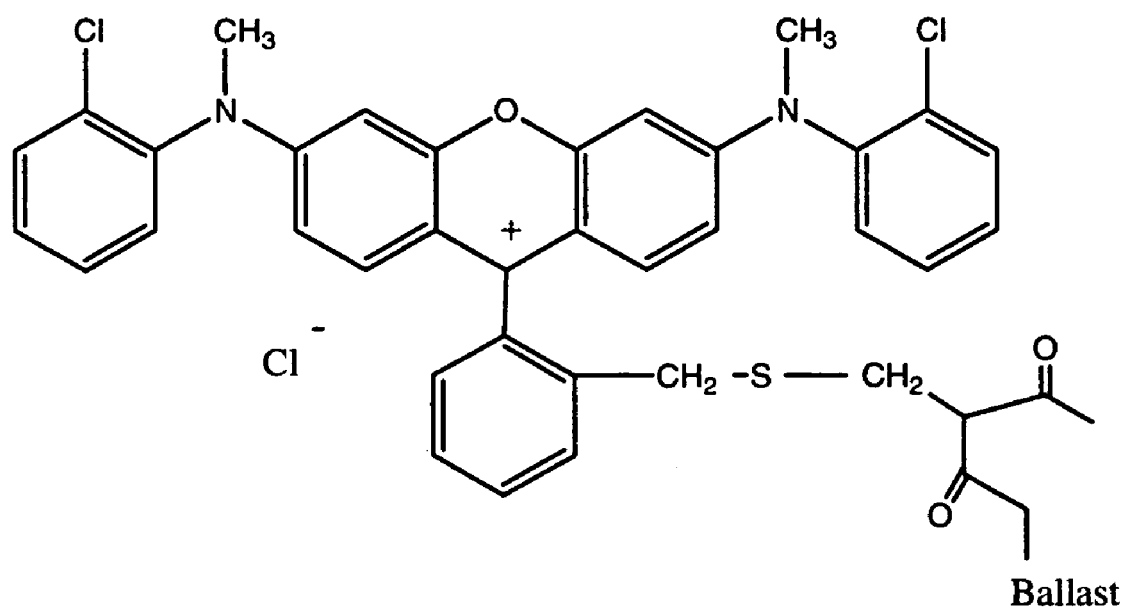
FIG. 7 depicts another colored compound suitable for the present invention, wherein a xanthene chromophore has attached to it a CH2 spacer group, which is attached to a sulfur nucleophile and attached to the nucleophile is a thermally activatable fragmentation group containing a ballast group.

FIG. 7 depicts an additional colored compound suitable for the present invention. In FIG. 7, a xanthene chromophore has attached to it a $CH_2$ spacer group, which is attached to a sulfur nucleophile and, attached to the nucleophile, is a thermally activatable fragmentation group containing a ballast group.

Figure 6:
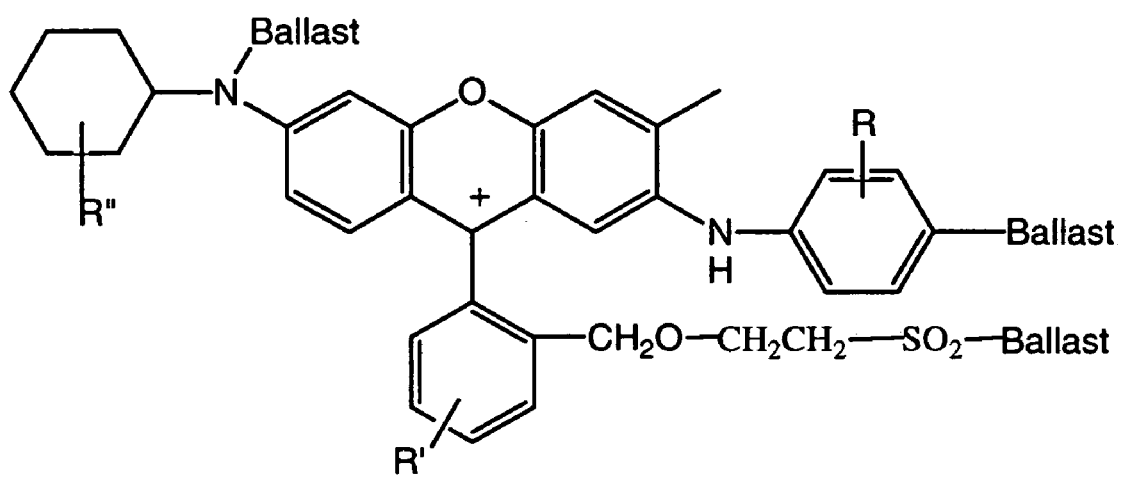
FIG. 6 depicts the structure of a functionalized colored compound containing ballast groups useful for the current invention.

It should be noted in FIGS. 6 and 7 that the ballast group that is attached to the FG fragmentation group would also allow the fragment to have certain predetermined properties such as, for example, improved biocompatibility or improved immobility, as well as, if desired, aiding in formulating the tissue marking composition. Ballast groups useful in the present invention include long chain fatty acids and fatty alcohols, gums, natural waxes, glycols, polyglycols, glycerol esters, gelatins, lipids, phospholipids, arabinogalactan, glutaraldehyde, petroleum wax, and mixtures thereof, poly (acrylic acid co-hypophosphorite) sodium salt, polyacrylamides, alginates, caseinates, polypectates, cellulosic materials, chitosan, glycerides, pectins, long chain polyacrylates, polymaleic acid and/or its sodium salts, polyvinyl acetate, sugars, polysorbate 80, polyvinylpolypyrrolidone, polyvinylpyrrolidone, and poly(20 vinylpyridine-co-styrene). poly(hexadecyl acrylamide), poly(butyl acrylate), poly (hexadecyl acrylate), poly(octadecyl acrylate), poly (dodecene), poly(isobutene), poly(trimethyl glutarate), polyanhydides, polyorthoesters, polystyrene, polyurethane, polypropylene, polymethacrylate, polytetrafluoroethylene, and other known polymers which are compatible with biological tissue. The ballast group can be chosen to be of a size that aids in immobilization, such as, for example, between 5 and 300 Angstroms as well as chosen to be of a type that can interface with the surrounding tissue to aid in immobilization, for example, by hydrogen bonding.

The colored compositions that result in tissue markings of the current invention includes at least one colored compound and at least one infrared absorbing compound and may be present in admixture with a liquid carrier, such as for example, alcohol, water or glycerin or other liquid carriers well know in the art or mixtures thereof, and may additionally be admixed with binders, or encapsulated to give the desired tissue marking., or as combinations thereof. The tissue marking, either in its colored or colorless form, is designed to remain indefinitely in the tissue.

As an admix with binders, the tissue marking of the current invention may include one or more binder materials which are present to help keep the dye and infrared absorbing compound in close proximity to each other such that the heat generated by the infrared absorption may transfer more efficiently to the thermally labile group. Typical binder materials include, for example, long chain fatty acids and fatty alcohols, gums, natural waxes, glycols, polyglycols, glycerol esters, gelatins, lipids, phospholipids, arabinogalactan, glutaraldehyde, petroleum wax, and mixtures thereof, poly(acrylic acid co-hypophosphorite) sodium salt, polyacrylamides, alginates, caseinates, polypectates, cellulosic materials, chitosan, glycerides, pectins, long chain polyacrylates, polymaleic acid and/or its sodium salts, polyvinyl acetate, sugars, polysorbate 80, polyvinylpolypyrrolidone, polyvinylpyrrolidone, and poly(20 vinylpyridine-co-styrene), poly(hexadecyl acrylamide), poly(butyl acrylate), poly(hexadecyl acrylate), poly (octadecyl acrylate), poly(dodecene), poly(isobutene), poly (trimethyl glutarate), polyanhydides, polyorthoesters, polystyrene, polyurethane, polypropylene, polymethacrylate, polytetrafluoroethylene, and other known polymers which will bind with the dye and infrared absorbing compound to keep them in close proximity.

The colored compositions that result in tissue markings of the current invention may also be in the form of an encapsulant, used to encapsulate, entrap, encase, complex, or, in general, incorporate the at least one colored compound and the at least one infrared absorbing compound. The encapsulating materials are chosen to be biocompatible with the body and are generally transparent to visible radiation so that the color of the dye is efficiently presented. The encapsulant is also chosen to be essentially transparent to infrared radiation so that, during the process for rendering the tissue marking colorless, most or all of the applied infrared radiation reaches the infrared absorbing compound. They can be designed to remain indefinitely in the tissue, for example, by making the tissue marking large enough to resist elimination from the tissue or by designing the vehicle to interact with the tissue, such as, for example, through chemical bonding. Vehicles useful in the current invention include organic polymers, waxes, ethylene glycols, silicon based polymers, hydrogels, liposomes and combinations thereof. Examples of suitable organic polymers include polyacrylates, polyurethanes, polyamides, polyimides, polyesters, polyethylene oxides, and combinations thereof. Examples of vehicles and methods of preparation useful to the current invention are disclosed in U.S. Pat. No. 6,013,122. It should be noted that the encapsulant is designed to remain intact during the process for rendering the tissue marking colorless.

The colored compositions that result in tissue markings tissue markings of the current invention as described above can be introduced either as an admixture with a liquid carrier, an admixture with binder materials, as an encapsulant, or combinations thereof, into the tissue by a procedure that consists of piercing the tissue with needles or similar instruments to introduce the tissue marking by an alternating pressure-suction action. Typical processes use tattooing equipment well known to the art, for example, an electromagnetic coil machine, a rotary application machine or a manual device. Non-invasive methods are also useful for application of the current inventive tissue markings, such as, for example, ultrasonic techniques which cause tissue to become more porous, as described in U.S. Pat. No. 5,445,611.

It should be noted that the tissue marking compositions of this invention are not required to be encapsulated for permanence. For such cases, by controlling the size of the colored composition particles, one can ensure permanence. Minute particles (less than 0.15 microns) will have a higher probability of removal by the biological processes of the body. Hence, by keeping the colored composition particles about in the range of 0.15 to 6 microns, a sufficient number of the particles will be retained to create a permanent visible tissue marking. For example, for the case of a skin marking, this implies that a sufficient number of the particles will be either engulfed by the phagocytic skin cells (such as fibroblasts and macrophages) or retained in the extracellular matrix.

The tissue markings of the current invention can be "removed", that is, become colorless by application of infrared radiation. The source of infrared radiation may generally be an infrared laser. Both the infrared radiation and the infrared absorbing compound are chosen so that the infrared radiation is optimally absorbed by the inventive tissue marking. The optimal spectral range for the laser is 800-1800 nm. This spectral range is suitable for this application since the body has minimal absorbing materials in this range. Energy absorbing substances present in the body are water, that absorbs at 1800 nm and greater, melanin which broadly absorbs up to about 1100 nm, but absorbs far less energy at wavelengths over 800 nm; and oxyhemoglobin which has a maximum absorbance in the range of 400 to 600 nm. Short, intense pulses of light are absorbed specifically by the infrared absorbing compound of the tissue marking of the current invention with minimal absorption by the surrounding tissue. Again, since the surrounding tissue is transparent to the infrared radiation, damage to the surrounding tissue can be minimized or eliminated. When the tissue marking is introduced as encapsulated ink, the method of rendering the ink colorless occurs without the disruption of the encapsulant, such that the fragments of the once colored compound, the infrared absorbing compound and any other materials present remain encapsulated in the skin.

It should be noted that since the infrared absorbing compound, the infrared radiation source and the thermally labile substituent all chosen independently from the colored compound of the inventive ink, the method of "removal" or rendering the ink colorless is independent of the colored compound. As a result, using the current method, tissue markings of any color can be rendered colorless using a single application of a single infrared radiation source, such as a laser.

EXAMPLES

Example 1

Colored Compound to Colorless Compound Through Thermal Fragmentation of the Colored Compound The magenta compound of FIG. 2A was admixed with acetone and placed onto a glass slide and the acetone was allowed to evaporate at ambient conditions. The slide was placed onto a hot plate heated to approximately 250° C. The magenta color of the dye disappeared within one minute. The slide was cooled and rinsed with acetone into a small beaker to collect the material on the slide. Performing TLC on silica gel of the materials rinsed from the glass slide confirmed that the magenta compound from FIG. 2A had been completely converted to the cyclized compound in FIG. 2B. (Rf of the magenta compound of FIG. 2A=0.2, the Rf of the compound of FIG. 2B=0.9).

Example 2

Colored Composition Containing Colored Compound and Binder to Colorless Composition Through Thermal Fragmentation of the Colored Compound 223 mgs of the magenta compound of FIG. 2A was admixed with 5.13 gms of acetone. 2.53 gms of this admix was added to 10.0 gms of a 15% w/w admix of PMMA (polymethylmethacrylate). The admix thus contains 0.11 gms of the magenta compound of FIG. 2A and 1.5 gms of PMMA. Three drawdowns of this admix were made on PET (polyethylene-terephthalate) film using #12, #15 and #20 wire-wound coating rods to give three different coating thicknesses. The PET films were allowed to dry at ambient conditions. The three strips of coated PET film were placed on a hot plate heated to approximately 250° C. The magenta color of each film disappeared within 2 minutes.

Example 3

Thermal Fragmentation of the Magenta Dye with Application of Infrared Radiation 100 mgs of IR 1065A (an infrared absorbing compound obtained from ADS, Inc of Quebec, Canada) was admixed with 1.06 gms of acetone. 1.68 gms of an admix of 223 mgs of the magenta compound of FIG. 2A and 5.13 gms of acetone was added to 6.1 gms of a 15% admixture of PMMA in acetone. The acetone admix of the IR dye was added to the PMMA/magenta admix. Three drawdowns of this admix were made on white reflective PET film using #12, #15 and #20 wire-wound coating rods to give three different coating thicknesses. The PET films were allowed to dry at ambient conditions. Reflection density measurements with a Greytag MacBeth Spectrolino Densitometer gave a reading of 1.99 $\log_{10}$ density at a wavelength of 570 nm. A strip of the #12 bar coating was placed approximately 2.5 inches in front of a collimated IR laser emitting at 980+/−15 nm. A 1 second pulse from the laser resulted in a uniformly colorless circle of approximately 3/16 inches in diameter in the magenta coating. The reflection density measurement after exposure to the IR laser was 0.26 $\log_{10}$ density units. It should be noted that the base density (the reflectance of the white reflective PET film was 0.06 $\log_{10}$ density units). Hence the laser exposure lowered the reflection density from 1.93 (1.99 minus 0.06) to 0.20 (0.26 minus 0.06), a reduction of approximately 90%. It should also be noted that a black density measurement of the sample after exposure using the same densitometer gave a reading of 0.26 $\log_{10}$ density units that is 0.20 $\log_{10}$ density units over the base.

What is claimed is:

1. A tissue marking comprising at least one colored compound comprising a thermally activatable fragmentation group and at least one infrared absorbing compound, wherein the at least one colored compound is capable of being rendered colorless by unimolecular fragmentation of the thermally activatable fragmentation group when the tissue marking is non-imagewise exposed by a source of infrared radiation.

2. The tissue marking of claim 1 wherein the at least one colored compound comprises the form of:

D-Sp-Nu-FG wherein D comprises a chromophore, Sp comprises an optional spacer group connecting the colored compound and a nucleophile Nu, Nu comprises a substituted or unsubstituted nucleophilic group and FG comprises the thermally activatable fragmentation.

3. The tissue marking of claim 2, wherein the chromophore D comprises at least one of a substituted or unsubstituted triarylmethane, a xanthene, a rhodamine, a fluoran, a azocarbocyanine, a benzylidene, a thiazin, an acridine or an aminoanthraquinone;

wherein the optional spacer group Sp comprises at least one of substituted or unsubstituted alkyl groups, cycloaliphatic groups or sulfur or phosphorus containing groups or their oxides;

wherein nucleophile group Nu comprises at least one substituted or unsubstituted, oxygen, sulfur, phosphorus, carbon, selenium, nitrogen or silicon, or oxides thereof; and wherein the thermally activatable fragmentation group FG comprises substituted or unsubstituted carbonates, carbamates, esters, lactams, lactones, amides, imides, oximes, sulfonates, sulfinates, sulfenates, phosphates, phosphonates, or —$R_2C$—$RHC$—Y, wherein R is the same or different and comprises substituted or unsubstituted alkyl, aryl, or aralkyl groups and wherein Y comprises an electron withdrawing group that is capable of fragmenting when a sufficient amount of thermal energy is applied; said electron withdrawing group comprising at least one of cyano, nitro, a sulfoxide, a carbonyl containing compound, or a sulfonamide.

4. A tissue marking comprising:

at least one colored compound comprising:

a thermally activatable fragmentation group; and at least one infrared absorbing compound;

wherein the at least one infrared absorbing compound comprises a cyanine, phthalocyanine, squarylium, azulenium, indophenol, naphthoquinone, or anthraquinone; and wherein the at least one colored compound is capable of being rendered colorless by unimolecular fragmentation of the thermally activatable fragmentation group when the tissue marking is non-imagewise exposed by a source of infrared radiation.

5. The tissue marking of claim 4, wherein the infrared absorbing compound is chosen such that its absorption is such that the surrounding tissue is substantially transparent to the radiation being absorbed by the compound and wherein the source of infrared radiation is a laser.

6. The tissue marking of claim 4, wherein the at least one colored compound further comprises one or more ballast groups attached to the dye, the thermally activatable fragmentation group or both.

7. The tissue marking of claim 4, further comprising a biocompatible binder material.

8. The tissue marking of claim 7, wherein the infrared absorbing compound is chosen such that its absorption is such that the surrounding tissue is substantially transparent to the radiation being absorbed by the compound and wherein the source of infrared radiation is a laser.

9. The tissue marking of claim 4, further comprising a biocompatible polymeric encapsulant to encapsulate the at least one colored compound and the at least one infrared absorbing compound.

10. The tissue marking of claim 9, wherein the infrared absorbing compound is chosen such that the surrounding tissue is substantially transparent to the radiation being absorbed by the compound.

* * * * *

UNITED STATES PATENT AND TRADEMARK OFFICE
CERTIFICATE OF CORRECTION

PATENT NO.        : 7,842,128 B2
APPLICATION NO.   : 11/898569
DATED             : November 30, 2010
INVENTOR(S)       : Satish Agrawal et al.

Page 1 of 1

It is certified that error appears in the above-identified patent and that said Letters Patent is hereby corrected as shown below:

On the Title page at (73), delete "Indicatior" and insert -- Indicator --

Column 13, line 39 (claim 3), delete "thiazin" and insert -- thiazine --

Signed and Sealed this
Twenty-fifth Day of January, 2011

David J. Kappos
*Director of the United States Patent and Trademark Office*